United States Patent
Holtzman et al.

(10) Patent No.: US 6,465,195 B2
(45) Date of Patent: Oct. 15, 2002

(54) PREDICTIVE DIAGNOSTIC FOR ALZHEIMER'S DISEASE

(75) Inventors: David M. Holtzman; Anne Fagan Niven, both of St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/753,130

(22) Filed: Dec. 29, 2000

(65) Prior Publication Data

US 2001/0044126 A1 Nov. 22, 2001

Related U.S. Application Data

(60) Provisional application No. 60/173,987, filed on Dec. 30, 1999.

(51) Int. Cl.[7] .......................... G01N 33/53; C12Q 1/00; A61K 38/00
(52) U.S. Cl. ........................... 435/7.1; 435/7.92; 435/4; 530/300; 530/324
(58) Field of Search ................................. 435/7.1, 7.92; 514/885; 530/350, 387.1

(56) References Cited

U.S. PATENT DOCUMENTS 6,114,133 A    9/2000   Seubert et al. ............. 435/7.94

OTHER PUBLICATIONS

Shoji et al., 1998, J. Neurological Sciences, vol. 158, pp. 134–140.*
Kanai et al., 1998, Ann. Neurology, vol. 44, pp. 17–26.*
Motter et al., 1995, vol. 38, No. 4, pp. 643–648.*
Borchelt et al., 1996, vol. 17, pp. 1005–1013.*
Andreas et al., 1999, Arch. Neurol., vol. 56, pp. 673–680.*
Tamaoka et al., 1994, J. Biol. Chemistry, vol. 269, No. 52, pp. 32721–32724.*
Clark, C.M., et al., *The Dementias*, Butterworth–Heinemann, Boston, Mass. (1998) 285–304.
Fagan, A.M. et al. Soc. Neurosci. Abstr., 29th Annual Meeting of the Society for Neuroscience, Miami Beach, Fl., Oct. 23–28, 1999, vol. 25, p1348. Abstract No. 543.2.
Galasko, D. (1998). *J Neural Transm.* 53:209–221.
Galasko, D. et al. (1998). *Arch. Neurol.* 55:537–545.
Growdon, J.H. (1999). *Arch Neurol* 56:281–283.
Ida, N., et al., (1996). *J. Biol. Chem.* 271:22908–22914.
Takanashi, T., et al.. (1997). *J. Neurol. Sci.* 145:41–47.
Trojanowski, J.Q. et al. (1998) *Neurobiol Aging* 19:109–116.
Urmoneit, B. et al. (1997). *Lab Invest* 77(2):157–166.

* cited by examiner

*Primary Examiner*—John Ulm
*Assistant Examiner*—Olga N. Chervyshev
(74) *Attorney, Agent, or Firm*—Morrison & Foerster LLP

(57) ABSTRACT

A diagnostic method for identifying individuals at risk for developing Alzheimer's disease is disclosed. The method relies on elevated levels of the ratio of $A\beta_{40}/A\beta_{42}$ associated with lipoproteins in the cerebrospinal fluid of individuals at risk as compared to this ratio in the overall population.

4 Claims, 4 Drawing Sheets

PREDICTIVE DIAGNOSTIC FOR ALZHEIMER'S DISEASE

CROSS-REFERENCE TO RELATED APPLICATIONS

This application claims priority under 35 U.S.C. § 119(e) from provisional application No. 60/173,987 filed Dec. 30, 1999 and incorporated herein by reference.

STATEMENT OF RIGHTS TO INVENTIONS MADE UNDER FEDERALLY SPONSORED RESEARCH

This invention was supported at least in part by an agency of the U.S. government under NIH-NIA grant P50-AG05681 and P50-AG00861. The U.S. government has certain rights in this invention.

TECHNICAL FIELD

The invention relates to a test that can be used to predict whether cognitively competent individuals are likely to develop Alzheimer's disease. More specifically, the invention relates to measurement of the ratio of amyloid protein β (Aβ)40 to Aβ42 in cerebrospinal fluid lipoprotein fractions as a predictor of this condition.

BACKGROUND ART

Alzheimer's disease (AD) is a highly troubling cause of dementia, especially in elderly people. Confirmation of the presence of AD is generally done post-mortem and the disease is characterized by neurofibrillary tangles and neuritic plaques. The diagnosis even of existing AD in patients is not always accurate and can only be confirmed by post-mortem analysis. Early diagnosis prior to the onset of dementia is essentially nonexistent although there are predictors of the disease which could most readily be characterized as risk factors. Among these risk factors is the presence of the E4 allele of apolipoprotein E (ApoE). In humans, ApoE has three isoforms (ApoE2, ApoE3 and ApoE4) that differ by only a single amino acid substitution. E4 ($Arg^{112}$, $Arg^{158}$) and E2 ($Cys^{112}$, $Cys^{158}$) are less common than E3 ($Cys^{112}$, $Arg^{158}$). ApoE is a major apolipoprotein constituent of cerebrospinal fluid (CSF) where it is associated with high density lipoprotein (HDL)-like particles. The ApoE in CSF is derived from the brain. Thus, an aberration in the ApoE component is logically related to neurological disease.

Growdon, J.H. in *Arch Neurol* (1999) 56:281–283 summarizes the status of antemortem diagnosis of AD. As reported, a working group convened in 1997 to evaluate this resulted in a consensus statement entitled "Molecular and Biochemical Markers of AD" which appeared in *Neurobiol Aging* (1998) 19:109–116. This study observed that no clinical biomarker has achieved universal acceptance.

Among the markers currently under consideration are those related to the proteins which account for the features found in Alzheimer brains postmortem. The neurofibrillary tangle is composed primarily of a hyperphosphorylated tau protein, a cytoskeletal protein. The neuritic plaque contains a core of amyloid protein, much of which is a 42-amino acid peptide ($A\beta_{42}$) derived from proteolytic cleavage of a larger precursor protein. Another form of this protein derived from the same precursor contains only 40 amino acids ($A\beta_{40}$). Blood tests based on these proteins do not seem to correlate well with AD.

Others have measured levels of these proteins in CSF. It appears that elevated levels of tau are present in CSF from AD patients (Clark, C.M., et al., *The Dementias*, Butterworth-Heinemann, Boston, Mass. (1998) 285–304). It has been shown that individuals with AD have decreased $A\beta_{42}$ levels in their cerebrospinal fluid (Galasko, D., et al, *Arch. Neurol.* (1998) 55:537–545; Ida, N., et al., *J. Biol. Chem.* (1996) 271:22908–22914; Kanai, M., et al., *Japan. Ann. Neurol.* (1998) 44:17–26; Motter, R., et al., *Ann. Neurol.* (1995) 38:643–648; Tamaoka, A., et al., *J. Nezirol. Sci.* (1997) 1997:41–45. The Motter paper indicated $A\beta_{42}$ levels in AD CSF were independent of ApoE genotype, but the larger study by Galasko showed an inverse relationship between the E4 allele and $A\beta_{42}$ levels. The Kanai paper reported an increase in $A\beta_{40}/A\beta_{42}$ levels in CSF from AD patients, but interpolation from regression analysis suggested that this increase begins prior to the onset of clinical symptoms. It has also been found that in AD patients, $A\beta_{42}$ levels in CSF are decreased, whereas the levels of total Aβ proteins ($A\beta_{42}+A\beta_{40}$) are substantially the same in AD patients and in normal controls (Motter, et al., Supra). The Growdon article (supra) concludes, however, that these alterations in tau and $A\beta_{42}$ do not occur with sufficient frequency and magnitude so that they offer diagnostic value.

Thus, at present, there appears to be no satisfactory diagnostic marker even for existing AD, much less a diagnostic predictor for an individual, who although exhibiting normal cognitive responses, will inevitably, or most likely, develop AD. The test described herein meets the need for such a diagnostic. Details of this test are described in an article by Fagan, A.M., et al., *Ann. Neurol.* (2000) 48:201–210, incorporated herein by reference.

DISCLOSURE OF THE INVENTION

The present invention offers a diagnostic method which identifies those individuals who will later in life be at higher risk for developing AD. The diagnostic is based on the surprising discovery that the lipoprotein fraction of CSF in such individuals has increased ratios of $A\beta_{40}$ to $A\beta_{42}$. Thus, the invention offers a relatively noninvasive and straightforward method to identify those individuals at high risk for subsequent development of AD. Although the ratio in the lipoprotein fraction is the most highly correlated with the probability of the onset of AD, the value of the ratio correlates strongly with the ratio in total CSF. Thus, although less reliable, total CSF could also be used as the substrate for this ratio determination.

Accordingly, in one aspect, the invention is directed to a method to identify an individual having an enhanced risk for development of AD, which method comprises determining the ratio of $A\beta_{40}$ to $A\beta_{42}$ preferably in the lipoprotein fraction of the CSF in said individual and comparing this ratio to the corresponding ratio in the population as a whole or to the ratio found in the CSF lipoprotein of a subgroup of the population not at risk for AD. If the subject is found to have an elevated ratio compared to these populations, that subject is at increased risk for developing Alzheimer's disease.

In other aspects, the invention is directed to kits containing suitable reagents for measurement of the $A\beta_{40}/A\beta_{42}$ ratio.

MODES OF CARRYING OUT THE INVENTION

Figure 1A:
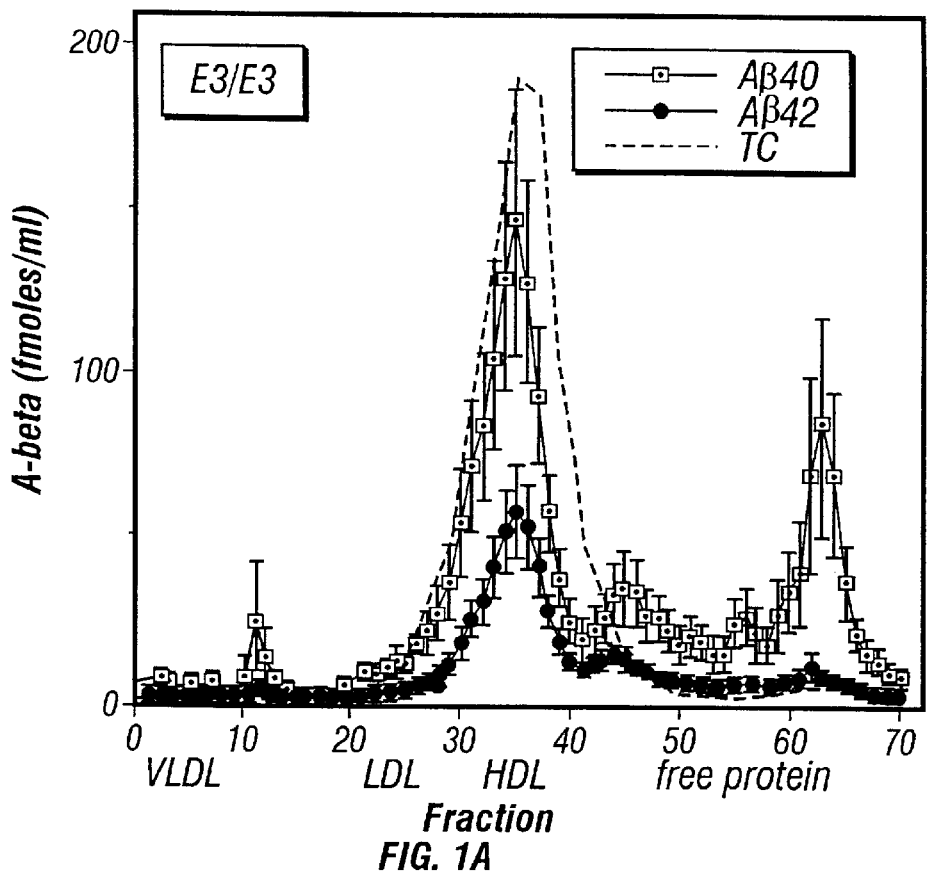
FIGS. 1A, 1B and 1C show the distribution of $A\beta_{40}$, $A\beta_{42}$ and total cholesterol in fractionated CSF from cognitively normal individuals of genotype E3/E3, E3/F4, and individuals with any E4 allele.

The lipoprotein fractions of cerebrospinal fluid are used as the basis for the diagnosis. In either total lipoproteins or in a specified subset of said lipoproteins, the levels of a $A\beta_{40}$ and $A\beta_{42}$ are measured in a subject to be tested. Any convenient method of measurement of these peptides can be used; antibodies are available which distinguish these forms of β amyloid protein and thus immunological assays are currently the most convenient. However, other methods for analysis could also be used, including immunoprecipitation, size separation, amino acid analysis, and the like. A wide variety of possibilities would be known to the ordinary practitioner, and should immunological tests be selected, a wide variety of formats is available.

Similarly, a number of methods are known to separate lipoprotein fractions from CSF or other body fluids. These methods include size separation using gel-filtration chromatography, as well as density centrifugation, affinity chromatography and non-denaturing immunoprecipitation, for example. For use in the method of the invention, all lipoprotein fractions can be combined as the test medium or a subset of the total lipoproteins may be used.

To perform the test, therefore, CSF is withdrawn from the subject using art-known methods, such as lumbar puncture. It may be helpful for the subjects to have fasted for several hours prior to the withdrawal of the fluid. Once the fluid is withdrawn, the lipoprotein fraction is isolated and the entire lipoprotein fraction or a portion of it is used in the assay. Suitable detection methods are then employed to measure the levels of $A\beta_{40}$ and $A\beta_{42}$ and the ratio is computed. The computed ratio is then compared with a suitable standard.

The standard $A\beta_{40}/A\beta_{42}$ ratio may represent the average of a suitable number of members of the general population, typically at least 10, more preferably 50, and still more preferably more than 100–500 members of the general population. The ratios for this sample are preferably determined using the same techniques as that employed for the subject. The standard for comparison may also be compiled using a sub-population at a somewhat lower risk for AD—such as individuals lacking E4 alleles. Determination of a suitable standard ratio for comparison to individual subjects is based on well known statistical parameters.

The ratio determined for the subject is then compared to the standard ratio whereby an elevated value in the individual as compared to the standard ratio identifies the subject as at risk for or destined to develop AD. Typically, the greater the deviation of the ratio in the individual subject from that in the "standard" population, the greater the risk for development of AD. Again, conventional statistics may be used to determine whether the difference determined in the individual from that of the standard population is significant.

Once a subject has been identified as at risk, suitable preventive and precautionary measures may be taken.

The reagents and equipment, if desired, for performing the diagnostic test of the invention may be prepared in kit form. The components of the kit will depend on the manner in which the $A\beta_{40}$ and $A\beta_{42}$ levels are measured; the kit may also contain control samples of these proteins as well as comparison charts reflecting standard values in the population and instructions for conducting the assays. The reagents will be packaged in suitable containers and may be formatted for ease of use.

Thus, a typical kit might include a container with antibodies specific for $A\beta_{42}$, a container containing antibodies specific for $A\beta_{40}$, additional components to permit use of these antibodies in an ELISA format, instructions for calculation of the ratio, and standard values for the ratio. The kit will typically also include samples of $A\beta_{40}$ and $A\beta_{42}$ as standards.

Applicants have found that the $A\beta_{40}/A\beta_{42}$ ratio identifies cognitively normal individuals at higher risk for Alzheimer's disease. While not intending to be bound by any theory, it is believed that the change in $A\beta_{40}/A\beta_{42}$ ratio in CSF lipoproteins may indicate changes in amyloid-β metabolism in the brain prior to the onset of clinical symptoms. Since the major constituent of amyloid plaques in the brain is $A\beta_{42}$, disappearance of this form from the lipoproteins of the CSF may indicate that $A\beta_{42}$ is being deposited in the brain itself and no longer be soluble.

Although a correlation with probability for onset of AD is clearly strongest with respect to the $A\beta_{40}/A\beta_{42}$ ratio in the lipoprotein fraction of CSF, this ratio also correlates well with the ratio in total CSF. This ratio is about 20 in unfractionated CSF and about 3 in the lipoprotein fractions; about 8% of the $A\beta_{42}$ contained in CSF, but only about 1% of $A\beta_{40}$ contained therein is found in the lipoprotein-containing fractions. The use of the lipoprotein-containing fraction to determine this ratio is thus a more reliable predictor than use of total CSF.

EXAMPLES

The following examples are intended to illustrate but not to limit the invention.

Example 1

Measurement of $A\beta_{40}$ and $A\beta_{42}$ in CSF Lipoproteins

A total of 25 human subjects, 14 females and 11 males were used in the study. Of these, 13 were E3/E3, 10 were E3/E4, and 2 were E4/E4. The analysis was performed by combining the latter two groups into a group designated "any E4." All of the subjects were age 50 or older, had no history of chronic medical disease, head trauma, stroke or other neurological problems and had a clinical dementia rating (CDR) of zero—i.e., were cognitively normal. CDR is measured by methods described by Berg, I., et al., *Arch. Neurol.* (1998) 55:326–335 and includes tests such as those described by Folstein, M.F., et al., *J. Psychiatr. Res.* (1 975) 12:189–198. The subjects were fasted for 12 hours before collection of the CSF; 35 ml of CSF were obtained from each subject through lumbar puncture (L4/L5) using a 20 gauge Spotte spinal needle. The samples were put on ice and centrifuged for five minutes at about 800× g. at 4° C. to pellet cellular elements and 30 ml of the supernatants were concentrated to 1 ml using Centriplus-10 concentrators (10 kD MW; Millipore, Bedford, Mass.). This removed proteins and other molecules of molecular weight less than 10 kD. The concentrates were fractionated by gel-filtration chromatography (BioLogic system; BioRad, Hercules, Calif.) using tandem Superose 6 HR 10/30 columns (Amersharn Pharmacia Biotech, Piscataway, N.J.) under physiological conditions (pH 7.4, ionic strength 0.15M NaCl with 0.001M EDTA). The methods employed optimize recovery of lipoproteins in their native form. Seventy fractions of about 400 µl each were collected from the gel-filtration chromatography and analyzed. Each of the fractions was analyzed for total cholesterol (TC), free cholesterol (FC), phospholipids (PL) and triglycerides (TG) using commercially available kits (Wako, Richmond, Va.). Cholesterol ester (CE) was measured as TC minus FC. The fractions containing lipoproteins were fractions 21–46. Fractions 30–40 are particularly rich in lipoproteins. Individual fractions were analyzed for $A\beta_{40}$ and $A\beta_{42}$ using an ELISA assay as described by Suzuki, et al., *Science* (1994) 264:1336–1340. This assay has a detection limit of about 1.5 fnol/ml. The results are shown in FIGS. 1A–1C.

Figure 1B:
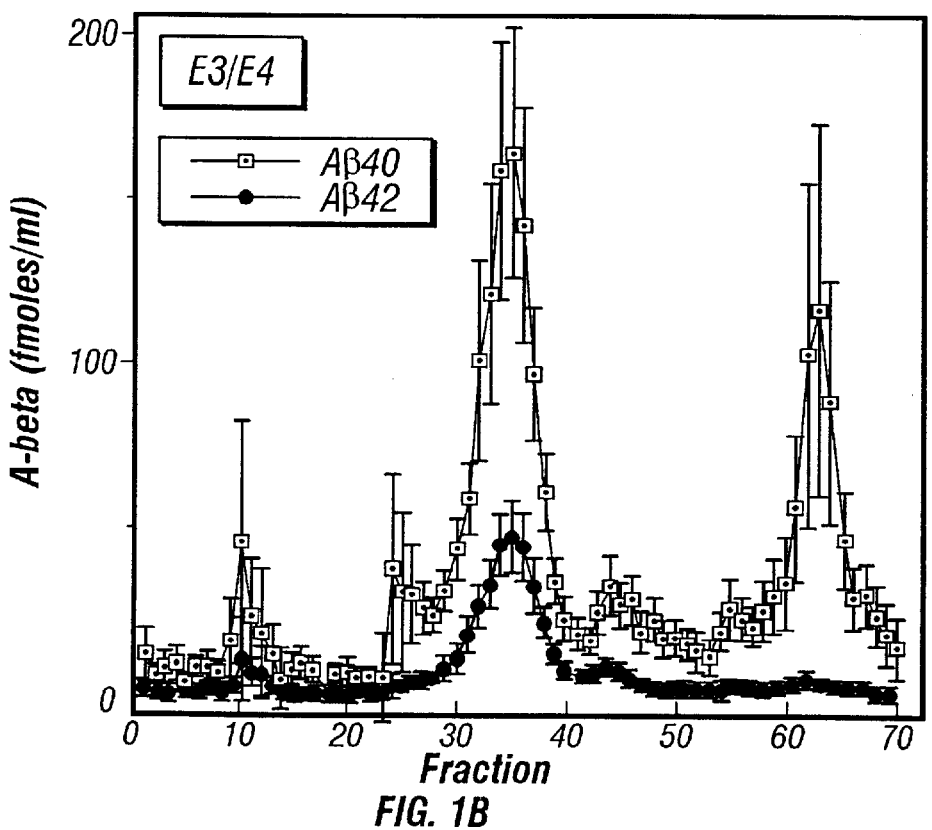
Figure 1C:
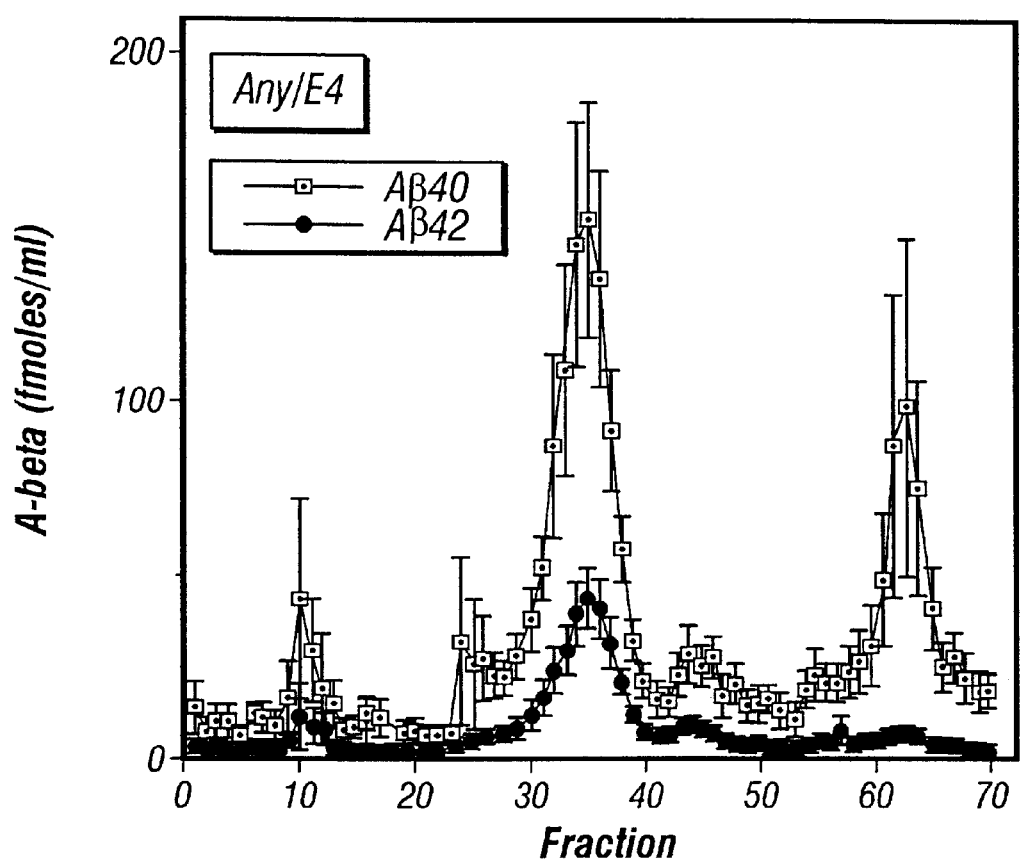

As shown in FIGS. 1A–1C, the pattern of elution of $A\beta$ proteins is similar in all genotypes. $A\beta_{40}$ elutes in a pattern indicating its association with CSF lipoproteins (fractions 30–40) as well as in lipid-poor fractions (fractions 40–50) and in lipid-free fractions (fractions 60–67). $A\beta_{42}$ is associated predominantly with the lipoprotein fraction (fractions 30–40). As shown in FIG. 1A–1C, the distribution pattern of these proteins did not appear to be affected by the apoE genotype of the individual.

Figure 2A:
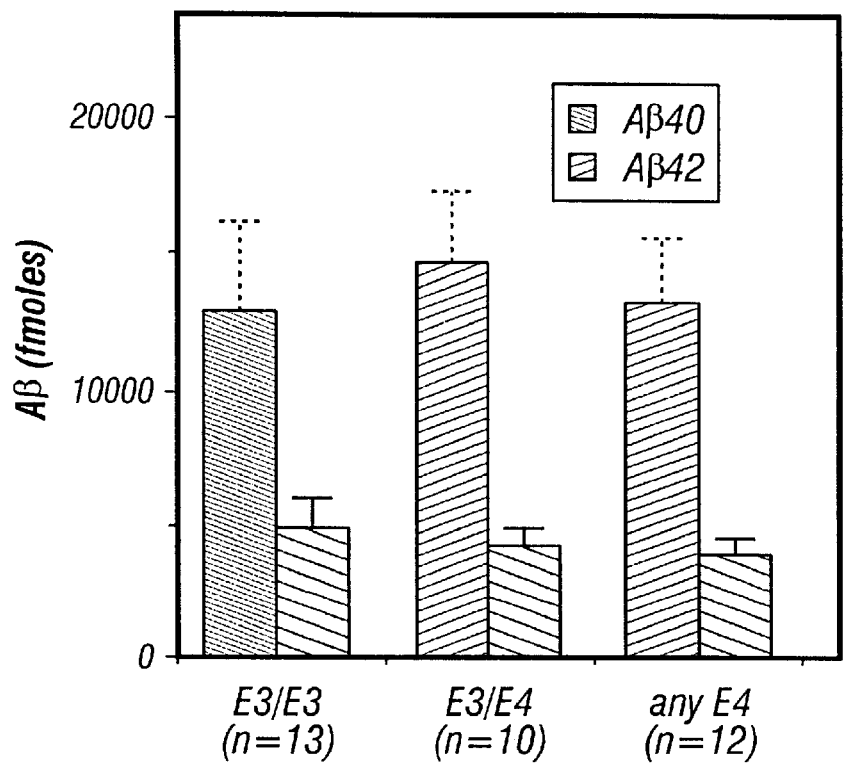
FIGS. 2A, 2B and 2C are graphical representations of the levels of $A\beta_{40}$ and $A\beta_{42}$ in the CSF lipoprotein fractions of individuals of various genotypes.
Figure 2B:
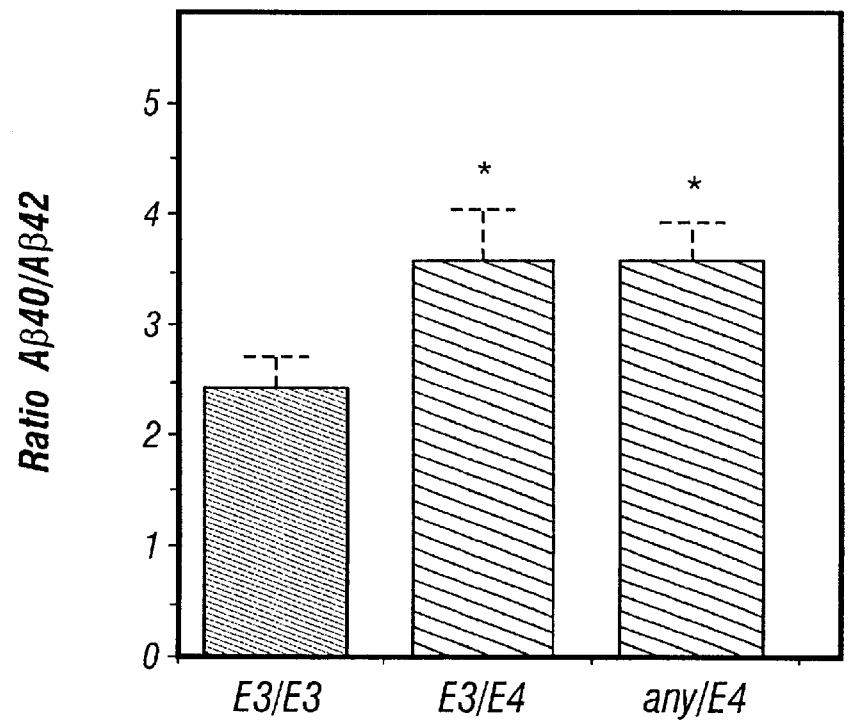
Figure 2C:
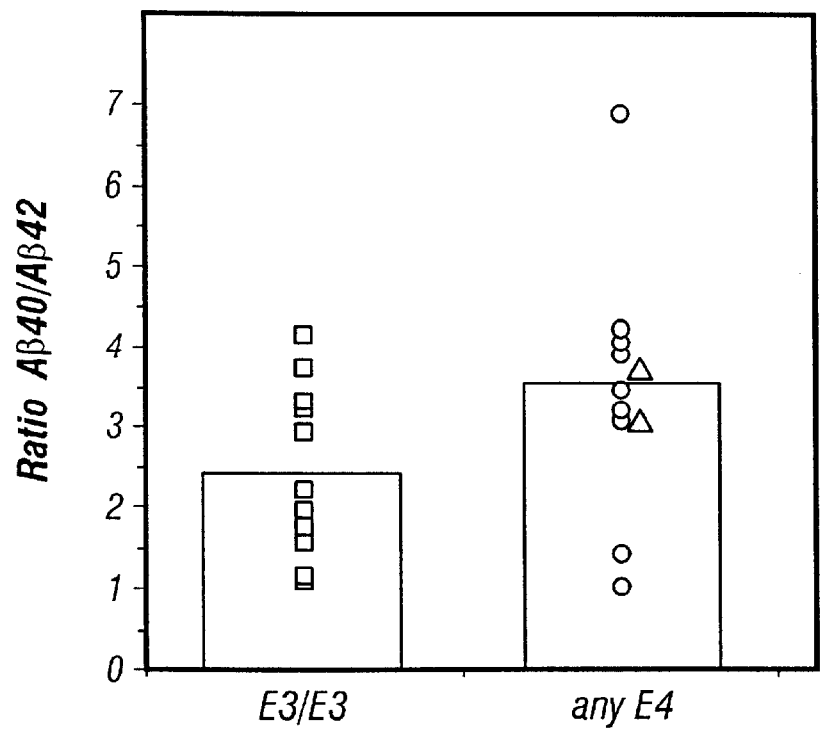

The results of determination of the $A\beta_{40}$ and $A\beta_{42}$ levels in the lipoprotein factions (fractions 21–46) are shown in FIG. 2. As shown in FIG. 2A, the absolute levels of these peptides did not appear to vary significantly depending on apoE genotype. However, FIG. 2B shows that the mean ratio of $A\beta_{40}$ to $A\beta_{42}$ in the lipoprotein fractions was significantly higher in subjects with an E4 allele. FIG. 2C is an alternative representation of these results indicating individual values as well as averages. As shown, the average ratio of $A\beta_{40}/A\beta_{42}$ in the lipoprotein fractions of individuals with any E4 allele was approximately 3.5 while the ratio in individuals not having an E4 allele was less than 2.5. Nevertheless, as shown in FIG. 2C, the values for individuals without an E4 allele varied from approximately 1 to 4.2 while those for individuals with an E4 allele varied from about 1 to the same level with one outlier at approximately 7. However, the proportion of individuals having high ratios in the group containing any E4 was much higher.

Figure 3:
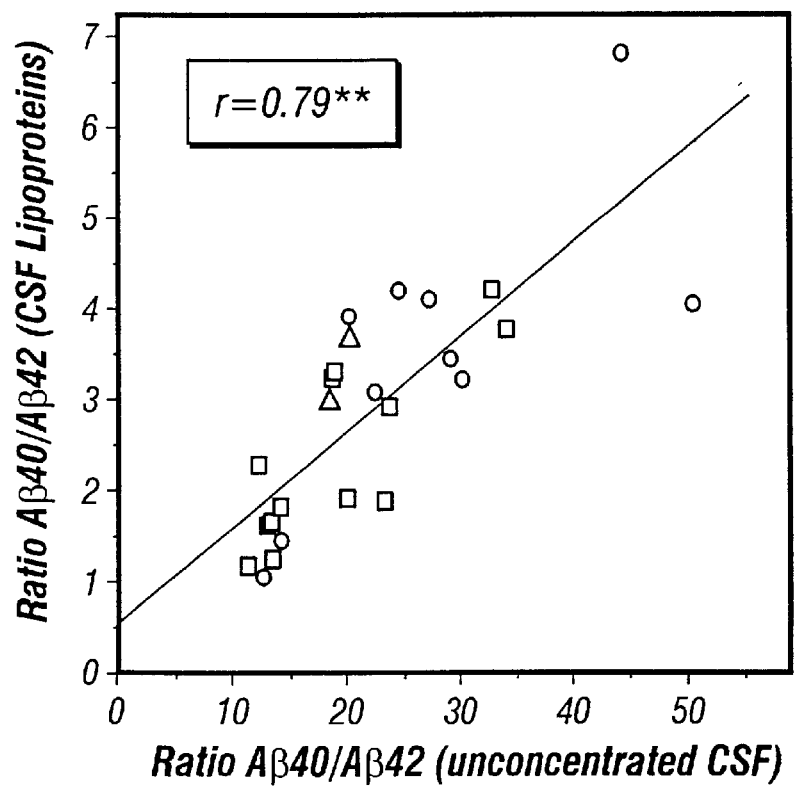
FIG. 3 shows the correlation between $A\beta_{40}/A\beta_{42}$ ratios in CSF lipoprotein fraction with the ratio in total CSF.

The results obtained for the lipoprotein fractions show a more distinctive correlation than the results obtained when the ratio of $A\beta_{40}$ to $A\beta_{42}$ was taken with respect to the concentrated CSF *per se*. There was an increased mean $A\beta_{40}/A\beta_{42}$ ratio in unfractionated CSF in E4-positive individuals; however, the trend just missed statistical significance. However, as shown in FIG. 3, the ratios were strongly correlated with the corresponding ratios in LP fractions.

The distribution of individual results is consistent with the fact that although E4 is a predictor of the probability of AD, it is not a causative agent. Thus, those subjects lacking an E4 allele, but who nevertheless have high ratios of $A\beta_{40}/A\beta_{42}$ may be destined for developing AD while those in the group with an E4 allele, but low ratio values may escape this condition. 38% of the subjects lacking an E4 allele had ratios within a range above 2.5 (the average for the E3/E3 population) and 17% of E4 positive subjects had ratios less than this value. Thus, the ratio may discriminate those individuals who will eventually develop the disease independent of ApoE genotype.

Example 2

Additional Parameters

The data set forth in the previous example are part of a more definitive study of the nature of CSF components in individuals with an E4 allele and those without.

As described above, in addition to measuring the $A\beta_{40}/A\beta_{42}$ ratio, other parameters were also measured. The results were also compared with data obtained from blood of the same subjects withdrawn at the same time and assessed for lipid analysis. The concentrations of serum TC and glycerol corrected TG's were measured using commercial kits (Bayer, Tarrytown, N.Y.; Roche Diagnostics, Indianapolis, Ind.). HDL cholesterol was measured as described by Warnick, G.R., et al., *Clin. Chem.* (1982) 28:1379–1388 and low density lipoprotein (LDL) cholesterol was calculated by the Friedewald equation. (Friedewald, W.T., *Clin. Chem.* (1972) 18:449–502).

In addition, serum and unfractionated CSF were analyzed for total protein using the bicinchoninic acid method (Pierce, Rockford, Ill.), for ApoE concentration by an ELISA assay as described by Fagin, A.M., et al., *J Biol. Chem.* (1999) 274:30001–30007 and for ApoAI concentration by Western blot followed by densitometry. Group differences were analyzed by Sudent T-tests and correlations assessed by linear regression analysis; significance was defined as $P<0.05$.

The results obtained in the study are summarized in Table 1. No statistical differences were observed in individuals possessing the ApoE4 allele in the levels of total protein, ApoE, or TC in CSF or of ApoE or of the lipid measures in serum. Neither did the level of ApoAI differ in CSF or serum for these individuals. The only parameter that differed statistically by gender was the level of HDL cholesterol.

With respect to the lipid profiles, including TC, FC, CE, PL's, and TG's, no correlation was observed with regard to these profiles in respect of individuals who possess or do not possess the E4 allele. Apolipoprotein distribution did not differ as a function of the genotype either.

Finally, the relationship of various lipoprotein measures in CSF and serum were compared. There was a significant correlation between CSF ApoE and CSF TC, but no relation between serum levels of ApoE and serum TC or between CSF ApoE and serum ApoE. ApoAI levels in CSF were strongly correlated with ApoAI levels in serum. There was no correlation between levels of TG's or TC's in serum and CSF. There was, however, a strong correlation between cholesterol levels in CSF LP's, which are HDL-like in size, and serum HDL's. The results suggest that although ApoE synthesis in the plasma does not significantly regulate CSF LP profiles, plasma ApoAI (the primary constituent of plasma HDL's) may influence CSF LP metabolism.

TABLE 1

Apolipoprotein E (ApoE) and Cholesterol Levels in Cerebrospinal Fluid and Serum Are Not Different in Normal, Fasted Individuals as a Function of ApoE Genotype

| ApoE Genotype | Age (yr) | Sex | MMSE | CSF protein (μg/ml) | CSF apoe (μg/ml) | CSF LP TC[a] (μg/30 ml CFS) | Serum apoE (μg/ml) |
|---|---|---|---|---|---|---|---|
| E3/E3 (n = 13) | 72.3 ± 1.5 | 3 M/10 F | 29.2 ± 0.2 | 774 ± 45.1 | 4.5 ± 0.6 | 72 ± 6.1 | 68 ± 9.1 |
| Any E4 (n = 12) | 73.6 ± 1.2 | 8 M/4 F | 29.3 ± 0.2 | 758 ± 33.2 | 5.3 ± 0.2 | 74 ± 5.6 | 51 ± 7.3 |
| Any E4 breakdown | | | | | | | |
| 3/4 (n = 10) | 74.5 ± 1.2 | 6 M/4 F | 29.2 ± 0.2 | 788 ± 28.0 | 5.3 ± 0.3 | 79 ± 5.0 | 51 ± 8.7 |
| 4/4 (n = 2) | 69.0 ± 0.0 | 2 M/0 F | 29.5 ± 0.5 | 608 ± 102.5 | 5.5 ± 0.2 | 47 ± 2.6 | 50 ± 12.6 |
| Sex | | | | | | | |
| Female (n = 14) | 73.4 ± 1.5 | | 29.3 ± 0.2 | 777 ± 43.0 | 4.8 ± 0.6 | 76 ± 5.8 | 65 ± 9.0 |
| Male (n = 11) | 72.4 ± 1.3 | | 29.1 ± 0.3 | 754 ± 33.7 | 5.0 ± 0.3 | 69 ± 5.6 | 54 ± 7.7 |

| ApoE Genotype | Serum TC (mg/dl) | LDL TC (mg/dl) | HOL TC (mg/dl) | Serum TG (mg/dl) |
|---|---|---|---|---|
| E3/E3 (n = 13) | 210 ± 10.3 | 129 ± 10.4 | 55 ± 4.4 | 127 ± 23.1 |
| Any E4 (n = 12) | 202 ± 6.8 | 132 ± 6.3 | 46 ± 4.1 | 116 ± 16.5 |
| Any E4 breakdown | | | | |
| 3/4 (n = 10) | 207 ± 6.6 | 137 ± 4.9 | 49 ± 4.2 | 104 ± 13.8 |
| 414 (n = 2) | 175 ± 13.5 | 109 ± 29.0 | 31 ± 1.5 | 177 ± 70.0 |
| Sex | | | | |
| Female (n = 14) | 214 ± 9.5 | 130 ± 9.2 | 58 ± 4.3[b] | 128 ± 21.9 |
| Male (n = 11) | 196 ± 6.7 | 131 ± 7.7 | 42 ± 3.1 | 114 ± 16.9 |

[a]Value for CSF lipoprotein total cholesterol (TC) was generated by summing TC values in fractions containing CSF lipoproteins (fractions 21–46).
[b]Statistically significant gender difference, $p < 0.05$.
HDL = high density lipoproteins; LDL = low-density lipoproteins; LP = lipoproteins; MMSE = Mini-Mental State Examination, where the range of scores can be from 30 (best performance) to 0 (worst performance); TC = total cholesterol; TG = triglycerides.

What is claimed is:

1. A method to identify a subject at risk for Alzheimer's disease (AD) which method comprises comparing the ratio of amyloid β peptide-40 ($A\beta_{40}$) to $A\beta_{42}$ in a lipoprotein fraction of the cerebrospinal fluid (CSF) of said subject with the ratio of $A\beta_{40}$ to $A\beta_{42}$ determined as a normal ratio, whereby a higher ratio of $A\beta_{40}/A\beta_{42}$ in said subject as compared to the normal ratio identifies said subject as at risk for Alzheimer's disease, and wherein said subject does not exhibit symptomology of AD.

2. A method to identify a subject at risk for Alzheimer's disease (AD) which method comprises
   (a) determining the ratio of $A\beta_{40}$ to $A\beta_{42}$ in a lipoprotein fraction of the CSF of said subject; and
   (b) comparing said ratio with the ratio of $A\beta_{40}$ to $A\beta_{42}$ determined as a normal ratio,
   whereby a higher ratio of $A\beta_{40}/A\beta_{42}$ in said subject as compared to the normal ratio identifies said subject as at risk for Alzheimer's disease; and
   wherein said subject does not exhibit symptomology of AD.

3. The method of claim 2 wherein said determining is performed by measuring the $A\beta_{40}$ and $A\beta_{42}$ concentrations in an immunoassay.

4. The method of claim 2 wherein said lipoprotein fraction is obtained by fractionating the CSF or a concentrate thereof by gel filtration chromatography.

* * * * *